United States Patent [19]

Sheingorn

[11] 4,253,470
[45] Mar. 3, 1981

[54] MARCUS-GUNN QUANTITATOR

[76] Inventor: Larry A. Sheingorn, 3139 Tennyson St., N.W., Washington, D.C. 20015

[21] Appl. No.: 3,512

[22] Filed: Jan. 15, 1979

[51] Int. Cl.³ .............................................. A61B 3/00
[52] U.S. Cl. .................................. 128/745; 128/25 A; 351/36
[58] Field of Search ................... 128/745, 25 A, 76.5; 351/2, 16, 39, 36

[56] References Cited

U.S. PATENT DOCUMENTS

| | | | |
|---|---|---|---|
| 2,160,359 | 5/1939 | Harper | 351/2 |
| 2,316,139 | 4/1943 | Wottring | 128/76.5 |
| 3,603,305 | 4/1969 | Oppenheimer | 128/76.5 |
| 3,936,162 | 2/1976 | Krakau et al. | 351/39 |

OTHER PUBLICATIONS

Schovten, J. F. et al., Measurements on Direct and Indirect Adapatation by Mean of a Binocular Method, 4/1939, J.D.S.A. vol.29 pp. 168-182.

Primary Examiner—Robert W. Michell
Assistant Examiner—Arthur S. Rose
Attorney, Agent, or Firm—Charles R. Wolfe, Jr.

[57] ABSTRACT

A device for quantitating afferent optic nerve defects is disclosed. The device is particularly adapted for use in examining optic nerve defects which produce a Marcus-Gunn pupil.

4 Claims, 5 Drawing Figures

MARCUS-GUNN QUANTITATOR

BACKGROUND OF THE INVENTION

1. Field of the Invention

The present invention is a device for quantitating afferent optic nerve defects which produce a Marcus-Gunn pupil.

2. Description of the Prior Art

Every ophthalmologist is familiar with the swinging flashlight test, where an ordinary light is first shown in one eye, then the other, then back again. In the normal patient, one observes a direct pupilary constriction in both eyes, as the light strikes each one in succession. In a patient with an afferent defect, however, the consensual constriction will be greater than the direct such that, when the light is moved towards the afferently-deficient eye from the intact eye, the former eye's direct response will be so much less than its consensual that its pupil will appear to dilate in response to the flashlight. This abnormality is termed the Marcus-Gunn effect and is a major diagnostic sign of afferent optic nerve defects.

At present, there are several methods for quantitatively measuring Marcus-Gunn phenomena. One method is to place a series of neutral density filters in front of the intact eye, and to repeat the swinging flashlight test. More particularly, this method is performed by rapidly increasing the density of the filters in front of the intact eye until the defective eye's consensual reflex is observed to be reduced to the same level as its impaired direct reflex. When this endpoint is reached, the eye with the afferent defect will show no dilation when the light illuminates it; i.e., its consensual reflex has been reduced to equal its direct.

Unfortunately, this method suffers from several disadvantages. For example, retinal bleaching poses a significant problem; since no filter is ever placed over the afferently-defective eye, that eye will gradually constrict more as more room light is constantly illuminating it. Hence, the observer quickly notes that, as the test proceeds, he must gradually increase the amount of absorption used in front of the intact eye to achieve the same endpoint. Clearly, retinal bleaching, which occurs in a matter of fractions of seconds, makes this method's reproducibility highly dependant on the dexterity of the physician.

SUMMARY OF THE INVENTION

Accordingly, it is a primary objective of the present invention to eliminate the limitations in conventional testing procedures for measuring afferent eye defects.

This objective is accomplished by a device comprising two lamps, each placed at the focal length of a small lens. The rays from each lamp are made parallel by each lens as they are shown into each eye. A mechanical frame holds the lamps as each beam shines in one eye. The device alternately blinks each lamp so that a period of time always exists in which both lamps are off, thus precisely simulating the swinging flashlight test. If a Marcus-Gunn pupil is observed in one eye the opposite lamp is dimmed with a knob on the device. The knob reduces the current through the lamp, and therefore reduces the illumination that the lamp provides. A sample and hold circuit stores and displays the illumination emitted by each lamp. When no dilation is observed, the display device is read and the reading recorded.

DETAILED DESCRIPTION OF THE INVENTION

Figure 1:
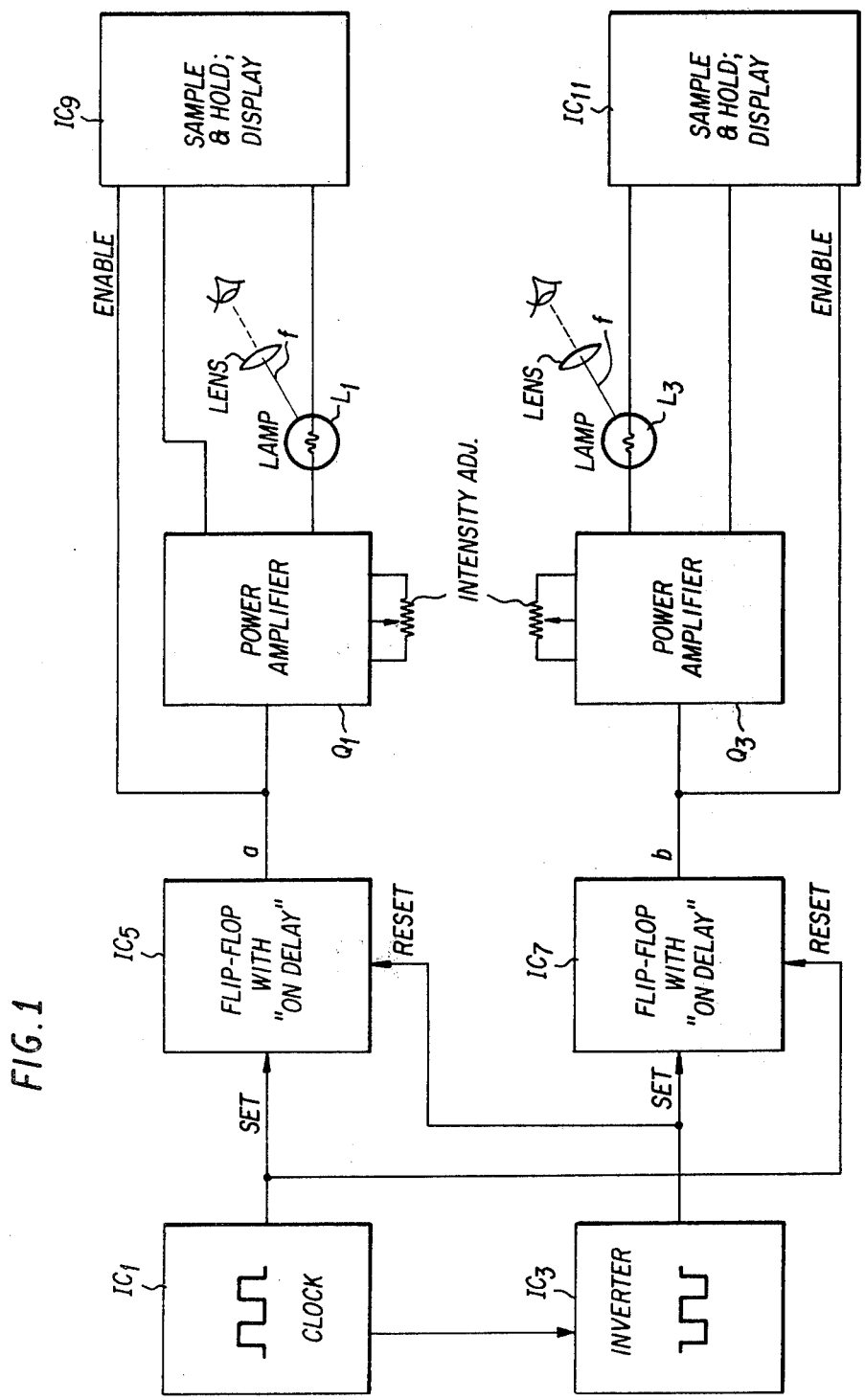
FIG. 1 is a functional diagram of the device of the invention.

Referring to FIG. 1, the device uses an astable multivibrator, IC1, whose output is connected to inverter IC3, bistable multivibrator IC5's set line, and bistable multivibrator IC7's reset line, as the system clock. With inverter IC's output connected to IC5's reset line, and IC5 and IC7's set delay circuitry appropriately chosen, this simple circuit produces the data stream on lines a and b, as shown in the timing diagram, FIGS. 2C and 2D.

Figure 2A:
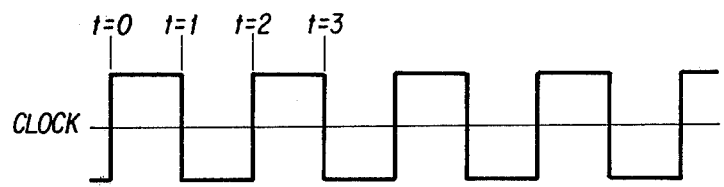
FIGS. 2a-2d represent the timing diagram for the device of the invention.
Figure 2B:
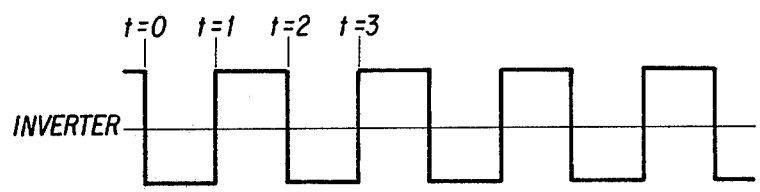
Figure 2C:
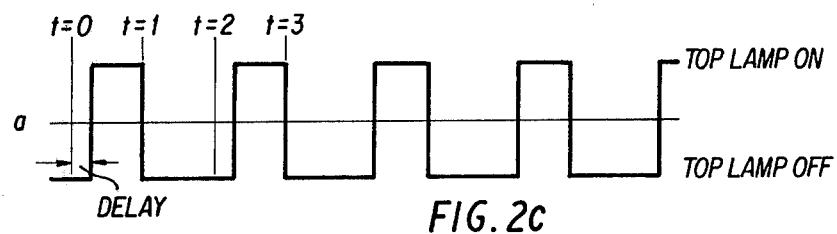
Figure 2D:
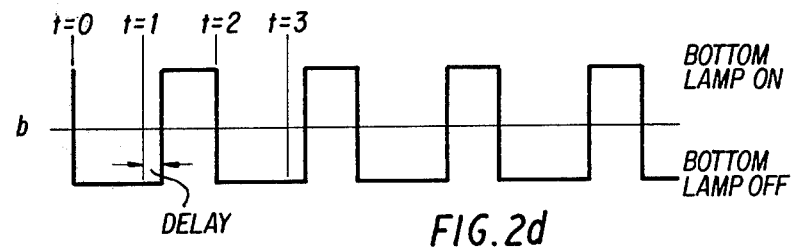

From the figures, it is clear that FIGS. 2C and 2D represent appropriately timed on/off states for each of their lamps. The data at each of the lines a and b is amplified by amplifiers Q1 and Q3, respectively. The gains of the amplifiers are controlled by the user during the test; the gain of the afferently defective eye's lamp being set, and left at, maximum.

The output of Q1 and Q3 are supplied to their respective lamps, L1 and L3. A quantitative reading of illumination is simply derived by sampling the current flowing through the lamp while the lamp is on, and storing that information while the lamp is off, thus making the information continuously available to the user. IC9 and IC11's circuitry does that here.

The illumination from each lamp is directed evenly on each eye via a small lens placed appropriately, such that no cross illumination occurs.

I claim:

1. A device for quantitating afferent optic nerve defects comprising:
    (a) two lamps, each lamp being positioned such that each beam from each lamp is capable of being directed at a different eye of a human patient;
    (b) means for alternately illuminating said lamps;
    (c) means for independently varying the intensity of illumination of said lamps; and
    (d) means for independently quantitating the intensity of each lamp, comprising circuitry which samples, stores and displays a variable proportional to the illumination emitted by each lamp.

2. The device as defined by claim 1, wherein said means (b) comprises:
    (i) a system clock;
    (ii) circuits which invert the clock signal;
    (iii) circuits to delay the clock and inverter signal;
    (iv) two bistable multivibrators which are set and reset by the clock inverter and delay signals; and
    (v) power amplifiers that drive the appropriate lamp in response to the state of their bistable multivibrator.

3. The device as defined by claim 1, wherein said means for independently varying the intensity of illumination of said lamps comprises a potentiometer and associated circuitry for each lamp.

4. The device as defined by claim 1, wherein said means for independently quantitating the intensity of each lamp comprises circuitry which samples and stores the current through each lamp.

* * * * *